United States Patent
Bruckert

(10) Patent No.: US 8,501,759 B2
(45) Date of Patent: Aug. 6, 2013

(54) USE OF FIBRATES

(75) Inventor: Eric Bruckert, Paris (FR)

(73) Assignee: Fournier Laboratories Ireland Limited, Dublin (IE)

( * ) Notice: Subject to any disclaimer, the term of this patent is extended or adjusted under 35 U.S.C. 154(b) by 35 days.

(21) Appl. No.: 13/143,152

(22) PCT Filed: Dec. 31, 2009

(86) PCT No.: PCT/EP2009/068046
§ 371 (c)(1),
(2), (4) Date: Sep. 23, 2011

(87) PCT Pub. No.: WO2010/076333
PCT Pub. Date: Jul. 8, 2010

(65) Prior Publication Data
US 2012/0035197 A1 Feb. 9, 2012

(30) Foreign Application Priority Data

Jan. 2, 2009 (EP) .................................. 09305001

(51) Int. Cl.
*A61K 31/505* (2006.01)
*A61K 31/47* (2006.01)
*A61K 31/40* (2006.01)
*A61K 31/35* (2006.01)
*A61K 31/235* (2006.01)
*A61K 31/205* (2006.01)

(52) U.S. Cl.
USPC ........... 514/275; 514/311; 514/419; 514/423; 514/460; 514/543; 514/555

(58) Field of Classification Search
USPC ................. 514/275, 311, 419, 423, 460, 543, 514/555
See application file for complete search history.

(56) References Cited

U.S. PATENT DOCUMENTS

| 5,145,684 | A | 9/1992 | Liversidge et al. |
| 6,277,405 | B1 | 8/2001 | Stamm et al. |
| 7,259,186 | B2 | 8/2007 | Cink et al. |
| 7,276,249 | B2 | 10/2007 | Ryde et al. |
| 7,363,076 | B2 | 4/2008 | Yun et al. |

FOREIGN PATENT DOCUMENTS

| WO | WO 03/075911 A1 | 9/2003 |
| WO | WO 2007/137103 A2 | 11/2007 |

OTHER PUBLICATIONS

Surell et al., "Evaluation of an ambulatory device, CID 102, in the diagnosis of obstructive sleep apnoea syndrome", Eur Respir J., 1995; 8 (5) pp. 795-800 (six (6) sheets).
FDA (U.S. Food and Drug Administration) files corresponding to the product TriCor® tablet 145 mg, http://www.accessdata.fda.gov/drugsatfda_docs/nda/2004/021656s000_TricorTOC.cfm, (one-hundred-fifty-nine (159) sheets).
FDA (U.S. Food and Drug Administration) flies corresponding to the product TriLipix®, http://www.accessdata.fda.gov/drugsatfda_docs/nda/2008/022224_trilipix_toc.cfm (seven-hundred-sixty-six (766) sheets).
H. Yaggi et al., "Obstructive sleep apnoea and stroke", Lancet Neurology, Jun. 1, 2004, pp. 333-342, vol. 3, No. 6, Lancet Publishing Group, London, GB, XP004810069.
Hideki Watanabe et al., "Effects of Telmisartan, Angiotensin II Receptor Blocker, on Endothelial Function and Aortic Stiffness in Morning Hypertensive Patients with the Metabolic Syndrome and Obstructive Sleep Apnea", Circulation, Nov. 12, 2008, p. 463, vol. 118, No. 18, Suppl. 2, Lippincott Williams & Wilkins, US, XP009116096.
Russell Conduit et al., "A neurotoxinological approach to the treatment of obstructive sleep apnoea", Sleep Medicine Reviews, W.B. Saunders, Sep. 11, 2007, pp. 361-375, vol. 11, No. 5, XP022237354.
International Search Report dated Mar. 16, 2010 (Four (4) pages).
PCT/ISA/237 Form (Seven (7) pages).

*Primary Examiner* — Raymond Henley, III.
(74) *Attorney, Agent, or Firm* — Crowell & Moring LLP

(57) ABSTRACT

The present invention, which is applicable in the pharmaceutical industry, relates to the use of fibrates, in particular fenofibrate, especially in the form of a solid oral composition, for the manufacture of a drug for the treatment of sleep apnea, sleep apnea syndrome, in particular obstructive sleep apnea or obstructive sleep apnea syndrome.

16 Claims, No Drawings

USE OF FIBRATES

FIELD OF THE INVENTION

The present invention generally relates to a novel therapeutical use of fibrates, in particular fenofibrate. More specifically, the present invention relates to the use of a fibrate for the preparation of a medicament useful for the treatment of sleep apnea and sleep apnea syndrome, in particular obstructive sleep apnea and obstructive sleep apnea syndrome.

BACKGROUND OF THE INVENTION

Sleep apnea is the cessation of breathing for at least 10 seconds, whereas 50% to 80% reduction in airflow for significant periods during sleep is called hypopnea. These events are accompanied with reduction in oxygen ($O_2$) saturation, increase in arterial pressure and decrease in heart rate. Apneic and hypopneic events are combined into the apneic/hypopneic index (AHI), which is the total number of apneic/hypopneic events per hour of sleep. AHI is usually of 10 or more in sleep apnea.

There are 3 types of sleep apnea: obstructive sleep apnea (OSA), central sleep apnea (CSA) and mixed sleep apnea which has both OSA and CSA as components.

Obstructive sleep apnea (OSA) is due to the occlusion of the airways leading to ineffective respiratory efforts during sleep. OSA is often associated with obesity. Its hallmark clinical symptom is excessive snoring which abruptly ceases during the apneic episodes and the brief period of patient arousal and then resumes when the patient again falls asleep. This may cause excessive daytime sleepiness that can lead to impairment of almost any daytime activity (sleep apnea syndrome).

Central sleep apnea (CSA), which is rare, is usually due to central nervous system dysfunction and causes no respiratory effort.

The most common treatment for patients with severe sleep apnea is continuous positive airway pressure (CPAP), usually through a nasal mask, during sleep. There is no evidence, apart from major weight reduction or abstinence from alcohol, that simple, non-invasive lifestyle changes improve sleep apnea or its consequences.

On the other hand, fibrates have been reported to lower plasma triglycerides and cholesterol levels and to be beneficial in the prevention of ischemic heart disease in individuals with elevated levels of LDL cholesterol. They can also decrease to some extent elevated fibrinogen and PAI-1 levels. Fibrate compounds can also elevate the level of plasma HDL cholesterol.

In the present invention, fibrates are defined as PPARα agonists (peroxisome proliferator activated receptor alpha agonists), including fibric acid derivatives (e.g. fenofibric acid or clofibric acid) and pharmaceutically acceptable salts and esters of such fibric acid derivatives.

Fibrate compounds include, but are not limited to, gemfibrozil, fenofibrate, bezafibrate, clofibrate, ciprofibrate, and analogs, derivatives and pharmaceutically acceptable salts thereof.

According to the present invention, the preferred fibrate is fenofibrate, fenofibric acid (active metabolite of fenofibrate) and/or a salt of fenofibric acid, in particular photostable salts of fenofibric acid as described in U.S. Pat. No. 7,259,186, especially choline, ethanolamine, diethanolamine, piperazine, calcium and tromethamine salts of fenofibric acid.

Fenofibrate has been commercially available in Europe (Lipanthyl®) since 1975 and in the USA (TriCor®) since 1998.

Fenofibrate is indicated as adjunct therapy to diet for the treatment of patients with primary hypercholesterolemia (Fredrickson Type IIa) or mixed dyslipidemia (Fredrickson Type IIb). Fenofibrate is also indicated as adjunctive therapy to diet for treatment of adult patient with hypertriglyceridemia (Fredrickson Types IV and V hyperlipidemia). The effects of fenofibrate observed in clinical practice have been explained in vivo in transgenic mice and in vitro in human hepatocyte cultures by the activation of peroxisome proliferator activated receptor α (PPARα). Through this mechanism, fenofibrate increases lipolysis and elimination of triglyceride-rich particles from plasma by activating lipoprotein ilipase and reducing production of apolipoprotein CIII (an inhibitor of lipoprotein lipase activity).

Fenofibrate also decreased plasma fibrinogen levels in normolipidemic patients and in dyslipidemic patients. The fibrinogen-lowering effect of fenofibrate was shown to be in the range −7% to −17%. This reduction of fibrinogen was accompanied by a reduction in other acute phase proteins such as interleukin 6 and C reactive protein.

Fenofibrate is virtually insoluble in water, which limits its absorption and contributes to a significant increase in exposure when administered with food. The absorption of fenofibrate, as currently marketed in Europe (tablets 160 mg and micronized capsules 67 mg, 200 mg and 267 mg dose strengths), is subject to substantial food effects. When the 160 mg tablet is administered with food, exposure to fenofibric acid, the active metabolite of fenofibrate, is increased by 35% compared to administration under fasting conditions. In order to improve convenience for patients, a fenofibrate tablet formulation has been developed which is devoid of food effect and may be taken without regard to meals. This new tablet formulation, based on a further reduction of fenofibrate particle size using a NanoCrystal® technology also allows a lower strength tablet (145 mg) to provide fenofibric acid exposure equivalent to that from the reference 200 mg micronized fenofibrate capsules and 160 mg tablet.

SUMMARY OF THE INVENTION

The present invention is based on the unexpected discovery that fibrates, in particular fenofibrate, lead to an improvement in most sleep apnea indices, in particular a reduction in number of obstructive apneas, and an increase in oxygen saturation during sleep as well as in attention tests on the next morning.

More precisely, the beneficial effect of fibrates on symptoms and biological changes associated with the sleep apnea syndrome has been demonstrated by a 1-month, randomized, double-blind, placebo-controlled study of fenofibrate 145 mg tablet in patients with sleep apnea syndrome.

In a first aspect, the present invention is therefore directed to the use of a fibrate, in particular fenofibrate, for the preparation of a medicament useful for the treatment of sleep apnea, sleep apnea syndrome, in particular obstructive sleep apnea and obstructive sleep apnea syndrome, and for improving vigilance.

In a second aspect, the present invention provides a method for treatment of sleep apnea, sleep apnea syndrome, in particular obstructive sleep apnea and obstructive sleep apnea syndrome, comprising administering a fibrate, in particular fenofibrate, to a subject in need thereof.

DETAILED DESCRIPTION

A further understanding of the nature and advantages of the present invention may be realized by reference to the remaining portions of the specification and claims.

Unless defined otherwise, all technical and scientific terms used herein have the same meaning as commonly understood by those of ordinary skill in the art to which this invention pertains.

In addition, the following definitions are provided to assist the reader in the practice of the invention.

The "subject" is preferably a mammal, more preferably a human.

The term "for the treatment" as used herein is to be understood as covering the direct use of the compound for the treatment of the specified disease.

The term "fibrate" will be used to denote both the fibric acid and the salified or esterified form of this compound.

Similarly, the term "fenofibrate" will be used to denote both the fenofibric acid and the salified or esterified form of this compound.

Within the framework of the present invention, the active substance can be therefore a fibric acid (e.g. fenofibric acid) as well as a pharmaceutically acceptable salt (e.g. salt of fenofibric acid, in particular a photostable salt such as a salt with choline or with ethanolamine, diethanolamine, piperazine, calcium, tromethamine) or ester (e.g. fenofibrate) of such fibric acid.

Any fibrate known and described in the art can be used in order to practice the use and method as described herein according to the present invention. Such fibrate compounds include, but are not limited to, fenofibrate, gemfibrozil, bezafibrate, clofibrate, ciprofibrate, and analogs, derivatives and pharmaceutically acceptable salts thereof.

Preferably, the fibrate is fenofibrate or a salt of fenofibric acid, in particular a photostable salt such as a salt with choline or with ethanolamine, diethanolamine, piperazine, calcium, tromethamine.

The fibrate according to the present invention can be directly administered under sterile conditions to the subject to be treated. The fibrate can also be administered as the active ingredient of a pharmaceutical composition or medicament.

Such pharmaceutical compositions typically comprise at least one fibrate together with one or more acceptable carriers thereof. Pharmaceutically carriers enhance or stabilize the composition, or facilitate preparation of the composition. Pharmaceutically acceptable carriers are determined in part by the particular composition being administered as well as by the particular method used to administer the composition. They should also be both pharmaceutically and physiologically acceptable in the sense of being compatible with the other ingredients and not injurious to the subject. Such carriers may take a wide variety of forms depending on the form of preparation desired for administration, e.g., oral, sublingual, nasal, or parenteral.

The pharmaceutical compositions can be prepared in various forms, such as granules, tablets, pills, capsules, suspensions and the like. The concentration of therapeutically active compound in the formulation may vary from about 0.1-100% by weight. These compositions are prepared by any methods well known in the art of pharmacy. They can be included in a container, pack, or dispenser together with instructions for administration.

In general, in the treatment of sleep apnea or sleep apnea syndrome, in particular of obstructive sleep apnea or obstructive sleep apnea syndrome according to the invention, the fibrate will be administered orally, especially in the form of tablet.

Thus, according to an advantageous embodiment, the medicament to be used for the use and method of the present invention, is in a form suitable for oral administration.

Particularly valuable results in the treatment of sleep apnea syndrome have been obtained according to the invention by the administration of a 145 mg NanoCrystal® tablet.

This galenical form and the process for its manufacture have been described in the FDA (U.S. Food and Drug Administration) files corresponding to the product TriCor® tablet 145 mg and information regarding the NanoCrystal® technology can be found in U.S. Pat. Nos. 5,145,684, 7,276,249 and 6,277,405, which are incorporated here by way of reference.

The use of fenofibrate in this galenical form is particularly valuable insofar as the safety of its use has been demonstrated in a large number of patients. The use of choline salt of fenofibric acid is particularly valuable as well insofar as the safety of its use has been demonstrated in a large number of patients (see the FDA (U.S. Food and Drug Administration) files relating to the product named TriLipix®.

The medicament of the present invention can be combined with or used in association with other therapeutic agents. For example, a subject may be treated with a fibrate, in particular fenofibrate, along with other conventional drugs. Examples of such known drugs include hydroxymethylglutaryl coenzyme A (HMG-CoA) reductase inhibitor or statin.

The use according to the invention therefore provides a medicament that can be used in association with a hydroxymethylglutaryl coenzyme A (HMG-CoA) reductase inhibitor or statin, such as, for example, pravastatin, lovastatin, simvastatin, atorvastatin, pitavastatin, rosuvastatin or fluvastatin.

Subjects suffering from sleep apnea or sleep apnea syndrome, in particular obstructive sleep apnea or obstructive sleep apnea syndrome are typically treated with pharmaceutical compositions of the present invention for a continued period of time (e.g., at least 30 days, 60 days, 90 days, or longer).

The pharmaceutical compositions comprise a pharmaceutically effective amount or prophylactically effective amount of a fibrate, in particular fenofibrate or a choline salt of fenofibric acid.

A suitable therapeutic dose can be determined by any of the well-known methods such as clinical studies on mammalian species to determine maximum tolerable dose and on normal human subjects to determine safe dosage.

In all use and method described herein, the medicament is preferably administered daily for at least 30 days. It can also be administered for at least 60 days, 90 days, or longer.

Preferably, when the active substance is fenofibrate, the daily dosage is of 45 to 235 mg, more preferably of 135 mg, expressed in fenofibric acid equivalent (145 mg of fenofibrate are equivalent to 135 mg of fenofibric acid). Otherwise stated, the medicament is used daily in an amount of fenofibrate that corresponds to a mass of fenofibric acid after hydrolysis of that amount of fenofibrate, of 45 to 235 mg, more preferably of 135 mg.

When the active substance is a fibrate, the medicament will be used in a daily dosage equivalent to 45 to 235 mg of fenofibric acid, preferably equivalent to 135 mg of fenofibric acid. In the following description, the following abbreviations and definitions of terms will be used:

Abbreviations

| Abbreviation | Full term |
|---|---|
| AE | adverse event |
| ALT (SGPT) | alanine aminotransferase |
| ANCOVA | analysis of covariance |
| AHI | apnea/hypopnea index |
| AST (SGOT) | aspartate aminotransferase |
| BMI | body mass index |
| bpm | beats per minute |
| CI | confidence interval |
| CK | creatine kinase |
| CPAP | continuous positive airway pressure |
| CSA | central sleep apnea |
| DBP | diastolic blood pressure |
| ESS | Epworth sleepiness scale |
| FAS | Full Analysis Set |
| HDL-C | high-density lipoprotein cholesterol |
| ICD9 | International Classification of Diseases 9th edition |
| LDL-C | Low-density lipoprotein cholesterol |
| LLN | lower limit of normal |
| Max | maximal value |
| Min | minimal value |
| N | total number of patients in a data set |
| n | number of patients in a data set for whom results were available |
| NCEP-ATPIII | National cholesterol education program-Adult treatment panel III |
| OSA | obstructive sleep apnea |
| PK | pharmacokinetics |
| PPARα | peroxisome proliferator activated receptor alpha |
| RBC | red blood cells |
| SAE | serious averse event |
| SD | standard deviation |
| SBP | systolic blood pressure |
| SpO$_2$ | Oxygen saturation of hemoglobin measured by pulse oximetry |
| TC | total cholesterol |
| TG | triglycerides |
| ULN | upper limit of normal |
| V1, V2, V3 | visit numbers |
| WBC | white blood cells |

Demonstration of the Effects of Fibrates in the Treatment of Sleep Apnea

1. CHARACTERISTICS OF THE POPULATION STUDDED AND STUDY DESIGN

The beneficial effects of fibrates in the treatment of sleep apnea syndrome were demonstrated by a 1-month, randomized, double-blind, placebo-controlled study of fenofibrate 145 mg tablet in patients with sleep apnea syndrome.

This study comprised 2 phases:

a run-in period of 1 to 5 weeks, on usual diet, a treatment period of at least 4 weeks (40 days maximum).

The study design can be represented diagrammatically as follows:

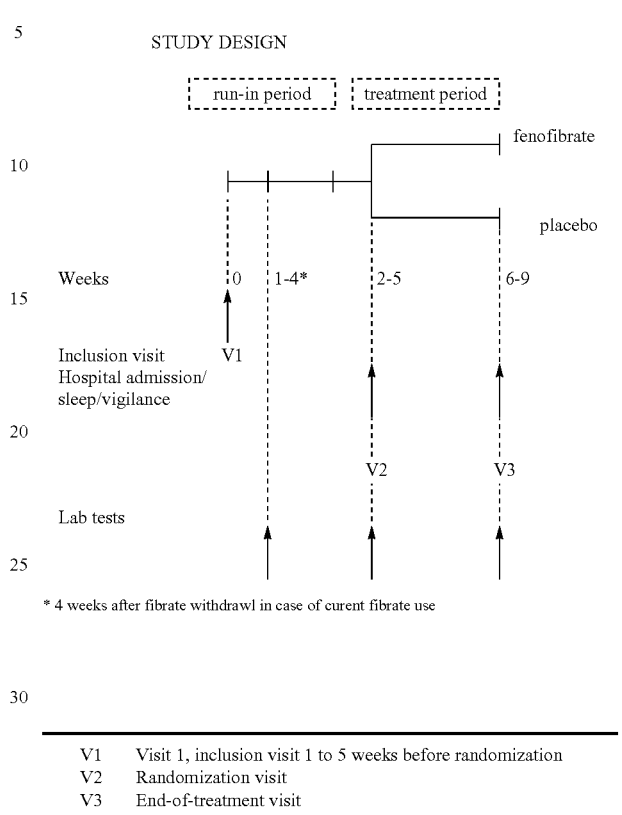

* 4 weeks after fibrate withdrawl in case of curent fibrate use

V1 Visit 1, inclusion visit 1 to 5 weeks before randomization
V2 Randomization visit
V3 End-of-treatment visit Patient Selection Patients fulfilling the following criteria have been included in the study:

both genders, from 18 to 70 years old, having previous diagnosis of sleep apnea not treated with CPAP or presenting clinical symptoms of sleep apnea, such as:

having reported to snore at home, on most if not all nights, or daytime sleepiness assessed through the Epworth sleepiness scale (a value>10 on this scale was to be considered as a clinical symptom of day time sleepiness), overweight or obese, with body mass index (BMI)≧25 kg/m$^2$ and <40 kg/m$^2$, known moderate hypertriglyceridemia, with fasting triglycerides (TG) level≧2.0 and <6.0 mmol/L within 3 months before the inclusion, confirmed by an inclusion laboratory test.

Thirty four (34) patients with sleep apnea syndrome were thus selected.

Run-In Period

Patients were to be on usual diet throughout the 1 to 5-week run-in period. Patients on fibrates at V1 (inclusion) and without any previous history of major hypertriglyceridemia or pancreatitis were to have stopped the treatment for 4 weeks before blood sampling.

Treatment Period

The treatment period was to last for at least 4 weeks (40 days maximum).

The patients were randomized to 1 of the 2 following treatment groups:

145 mg NanoCrystal® fenofibrate tablet, fenofibrate-matching placebo tablet.

Selection of Doses in the Study

The selected dosage for fenofibrate in this study was the no-food effect 145-mg NanoCrystal® tablet. This tablet had been shown to be bioequivalent to the 200 mg fenofibrate capsule and to the 160 mg fenofibrate tablet.

This dosage taken once daily is the standard dose used in the treatment of dyslipidemia.

Selection and Timing of Dose for Each Patient

During the 4 weeks of the treatment period, the patients were to take orally 1 tablet of 145 mg NanoCrystal® fenofibrate (active or placebo) in the morning with or without the meal.

Prior and Concomitant Therapy

The usual medications taken by the patients were not to be changed during the study. Treatment with statins were allowed provided that the dosage remained unchanged throughout the study.

Health Advice

The patients were asked not to change their usual diet throughout the study.

The efficacy of the treatment has been evaluated using the following variables:

Primary variables: number of obstructive apneas, of central apneas, of mixed apneas, total number of apneas, index of apnea per sleep hour, total number of hypopneas, index of hypopnea per sleep hour, index of apnea/hypopnea per sleep hour, total number of desaturations per sleep hour (with a variation of at least 3-4%), and percentage of time spent with $SpO_2$<90%.

Variables assessed as complementary analyses: cumulated duration of apnea, mean duration of apnea, duration of the longest apnea, number of non cortical micro-awakening indicators related to respiratory events/hour, number of non cortical micro-awakening indicators related to respiratory events, oxygen saturation in blood measured by pulse oximetry ($SpO_2$) in wake state, mean $SpO_2$ on sleep recording, minimum value of $SpO_2$, percentage of time spent with $SpO_2$<80%, percentage of time spent with $SpO_2$<85%, number of tachycardia, mean duration of tachycardia, number of bradycardia, mean duration of bradycardia, mean pulse rate, standard deviation pulse rate, minimum pulse rate, maximum pulse rate, decrease in daytime sleepiness assessed by the ESS, vigilance tests (reflexive visually guided saccades, antisaccades and sustained attention test).

Secondary variables: % change from baseline (V2) in fasting and post-prandial TG, total cholesterol (TC), high-density lipoprotein cholesterol (HDL-C), fasting plasma glucose (FPG), fibrinogen and insulin.

Plasma Study Drug Concentration:

Blood was collected for measurement of fenofibric acid at V2, pre-dose in the morning after the first sleep study, and at V3, pre-dose (24 h after last study drug intake) and 4 h after study drug intake, with breakfast, after the second sleep study.

Safety:

Analysis of safety included change in alanine aminotransferase (ALT), aspartate aminotransferase (AST), creatine kinase (CK), creatinine, white blood cell (WBC) and differential count, red blood cells (RBC), hemoglobin, hematocrit and platelets. Incidence of adverse events (AEs), serious or not, related to study drug or not, experienced during the treatment period.

The following procedures have been used for evaluating the above mentioned variables:

Determination of Apnea/Hypopnea Index (AHI)

Throughout the night, respiration was monitored by a sound pressure transducer placed on the suprasternal notch facing the trachea or thoracic strain gauges (model CID 102) (Van Surell C, Lemaigre D, Leroy M, Foucher A, Hagenmuller M P, Raffestin B. Evaluation of an ambulatory device, CID 102, in the diagnosis of obstructive sleep apnea syndrome. Eur Respir J. 1995; 8(5):795-800).

Apnea is defined as an absence of inspiratory flow for at least 10 seconds.

Hypopnea is defined as a 50% to 80% reduction in airflow combined with 3-4% oxygen desaturations.

Sleep apneas are classified as obstructive or central.

Central apneas are defined as total absence of inspiratory flow and chest/abdominal movement during the period of absence of inspiration flow.

Obstructive sleep apneas are defined by a decrease in airflow of more than 80% in the presence of paradoxical movements of the ribcage and abdomen. Similar to AHI, the obstructive and central apneas were based on definitions that require events to be associated with 3-4% desaturations.

Percent sleep time<90% $O_2$ saturation

Desaturation episodes were the markers of respiratory impairment. All-night recordings of arterial oxygen saturation were obtained using a cardio-respiratory pulse oximeter attached to the finger ($SpO_2$).

Severity of obstructive sleep apnea was measured by the number of falls in $SpO_2$ of more than 3-4% per hour of sleep. The equipment automatically selected the desaturation threshold (3 or 4%) according to the baseline $SpO_2$ value. To further define the severity of OSA, the lowest $SpO_2$ point and the percentage of time spent with $SpO_2$<90% was determined.

Heart Rate Recording

The number and mean duration of tachycardia and bradycardia were recorded throughout the sleep study.

Tachycardia was defined as a rate>90 beats per minute (bpm), bradycardia as a rate<50 beats per minute (bpm).

The Epworth Sleepiness Scale (ESS)

This scale is the most widely index used to measure sleep apnea subjectively. It is a self-administered questionnaire that asks patients their likelihood of falling asleep in 8 situations ranked from 0 (no chance of dozing), 1 (slight chance of dozing), 2 (moderate chance of dozing) to 3 (high chance of dozing). The numbers are then added together to obtain a global score between 0 and 24. A value of 10 or below is considered normal.

Computerized Attention/Vigilance Tests

All the 3 tests were performed in complete darkness in the morning after the sleep recording. The patient was seated 1 meter in front of a ramp, the head immobilized at the temples with a headrest. Eye movements were recorded by using horizontal electro-oculography with bitemporal electrodes. Manual reaction times were obtained by pressing on a button placed in front of the patient. Data are stored and analyzed after the tests.

Reflexive Visually Guided Saccades

Reflexive guided saccades were realized with a gap paradigm. Patients were instructed to initially stare at a central target that was illuminated for 2.5 to 3.5 seconds, then to make a eye movement (saccade) towards a 25° lateral target that appeared randomly right or left after the extinction of the central fixation point. This was performed by blocks of 12 targets (6 on the right and 6 on the left). The main parameter analyzed was the saccade latency, which is the reaction time between the appearance of the target and the start of the saccade towards this target. This test was to be repeated 4 times, i.e, 48 latency values.

Antisaccades

The same stimulus condition as in the visually guided saccade task was used, but patients were instructed to look, as quickly as possible, in the direction opposite to the peripheral target, i.e, to perform an antisaccade, without instructions about saccade amplitude. This test implies an active partici pation of the patient and requires a high level of attention. This was to be performed by blocks of 12 targets (6 on the right and 6 on the left) and the test was repeated 4 times, i.e, 48 latency values. The measured parameters were the anti-saccade latency and the percentage of errors (saccades made by mistake in direction of the target).

Sustained Attention Test

Patients were instructed to stare at a central point. Pairs of lateral targets appeared successively on the ramp. Both targets of each pair were equidistant from the middle of the ramp. They appeared most often near the middle (one at 10° on the left, the other one at 10° on the right) and more rarely far from the middle (one at 25° on the left, the other one at 25° on the right). The patients were instructed to press a button, as soon as they saw a pair of distant targets.

The measured parameters were the manual reaction time and the percentage of errors (responses for close targets and no response for distant targets). Optimal responses were obtained if the patients were able to have a high level of sustained attention during all the duration of the test. Each block of this paradigm included 10 pairs of distant targets. This test was repeated 5 times, i.e, 50 values for reaction time.

The tests were overviewed by trained staff. They were carried-out on the morning for about half an hour, whenever possible with the same timing at V2 and V3.

Laboratory Tests

TC, TG, HDL-C, glucose, fibrinogen and insulin were measured at inclusion and during the 2 hospital admissions before a lipid rich breakfast. Insulin was also measured before the lipid rich breakfast, each morning following the sleep study.

Post-prandial TG were measured 4 hours after a lipid rich breakfast.

Drug Concentration Measurements

Blood samples were collected on V2 morning on fasting state (24 hours after the last study drug intake) and on V3 on fasting state and on post-prandial state (4 hours after breakfast).

Concentrations of fenofibric acid (active metabolite of fenofibrate) in plasma were determined by High Performance Liquid Chromatography with ultra-violet (UV) detection. The lower limit of quantification (LLOQ) was 0.030 µg/mL.

2. STATISTICAL ANALYSIS

Raw values at baseline and V3 and absolute and % changes from baseline are provided for the variables analyzed in a continuous way, and frequencies at V3 are provided for the criteria analyzed in a categorical way.

Inferential statistics done depended on whether data were normally distributed or not.

If baseline data were normally distributed (Shapiro-Wilk test), an ANCOVA with the baseline value as covariate and the treatment effect as main factor was performed on V3 (end of treatment) data. The Least Square mean (LS-mean) of the difference fenofibrate—placebo at V3 with associated 95% confidence interval (CI) was provided.

If baseline data were not normally distributed (Shapiro-Wilk test), they were Log-transformed. If normality was then reached, the ANCOVA was performed on Log-transformed V3 data. The relative difference fenofibrate—placebo at V3 with associated 95% CI was provided.

If Log-transformed baseline data were not normally distributed (Shapiro-Wilk test), the 2 groups were compared at baseline and at V3 with the Wilcoxon test. No adjustment for multiplicity was done.

Complementary analyses included parametric (Pearson) and non parametric (Spearman) correlations between sleep study variables and V3 values or changes in fasting and post-prandial in TG.

3. RESULTS

Demographic and Other Baseline Characteristics

The mean age of patients (12 women and 22 men) was 55.6 years.

Their mean BMI value was 33.8 kg/m² and their mean waist circumference value was 111.4 cm.

Most of the patients had obstructive/central/mixed sleep apnea or obstructive/mixed sleep apnea.

During all the study, 16 patients (47%) received a concomitant statine treatment.

Recordings of the first night of the sleep study at V2 (baseline) allowed to establish the presence of sleep apnea (AHI higher than 10).

Median values of main efficacy criteria at baseline are presented in Table 1 below.

TABLE 1

| | |
|---|---|
| Number of apneas | 36.0 |
| Number of hypopneas | 82.0 |
| Number of desaturations | 179.0 |
| Number of central apneas | 3.0 |
| Number of mixed apneas | 3.0 |
| Number of obstructive apneas | 20.0 |
| Index of apnea/hypopnea/h | 21.0 |
| Index of apnea/h | 5.0 |
| Index of hypopnea/h | 13.0 |
| Percentage of time with SpO2 <90% | 10.0 |

Number = total number during sleep recording.
Index = number per hour of sleep recording.

The median duration of apnea was 13 seconds and the median cumulated duration during the overnight sleep study was 8 minutes.

The median value of apnea/hypopnea index was 21.0 episodes per hour.

The median number of non-cortical micro-awakening indicators related to respiratory events was 24 per hour.

The $SpO_2$ recorded during sleep was 93.0% (median), with a minimal value of 76.0%. The percentage of time with $SpO_2$<90% varied between 0 and 70%, that with $SpO_2$<85% varied between 0.0 and 14.0% (median: 1.0%), that with $SpO_2$<80% varied between 0.0 and 9.0% (median: 0.0%).

The median number of tachycardia (>90 bpm) episodes was 3.0 and the median number of bradycardia (<50 bpm) was 6.0, with a duration (median) of 10.5 and 9.0 seconds, respectively.

The mean pulse rate was 64.0 bpm (minimum: 49.0 bpm, maximum: 95.0 bpm).

The median score on the ESS was 8.0.

Computerized attention and vigilance tests were considered as normal or near normal.

Mean (SD) and median values of laboratory efficacy variables at baseline are presented in Table 2:

TABLE 2

| Fasting TG (mmol/L) | Post-prandial TG (mmol/L) | TC (mmol/L) | HDL-C (mmol/L) | Fasting glucose (mmol/L) | Fibrinogen (µmol/L) | Insulin (pmol/L) |
|---|---|---|---|---|---|---|
| 3.47 (2.08) | 5.52 (2.69) | 5.65 (1.34) | 1.04 (0.25) | 5.70 (0.92) | 10.88 (2.48) | 94.8 (43.1) |
| 2.50 | 4.60 | 5.66 | 0.99 | 5.60 | 10.29 | 82.9 |

Fasting and post-prandial TG values were in the moderately to severely elevated ranges. Mean and median TC values were in the elevated range according to the NCEP-ATPIII classification. HDL-C was close to normal in most of the patients. Mean and median values for FPG, fibrinogen and insulin were in normal range.

Efficacy Results:
Main Efficacy Analysis on the Primary Efficacy Criteria

All the primary efficacy variables were non-normally distributed at baseline. Except for the percentage of time with $SPO_2 < 90\%$, normality was achieved after Log-transformation. Then, the comparison between groups was performed with the ANCOVA on Log-transformed end-of-treatment (V3) values.

The results are presented in Table 3.

TABLE 3

| | Placebo | | Fenofibrate 145 mg | | Fenofibrate-Placebo at end of treatment | |
|---|---|---|---|---|---|---|
| | Base. | End (V3) | Base. | End (V3) | | |
| Variables | (median) | (median) | (median) | (median) | Estimate [95% CI] | p |
| Number of apneas | 36.0 | 31.0 | 34.0 | 20.5 | −35% [−66%; 27%] | 0.199 |
| Number of hypopneas | 94.0 | 69.5 | 76.0 | 63.0 | −46% [−75%; 17%] | 0.114 |
| Number of desaturations | 238.0 | 171.0 | 174.0 | 130.0 | −23% [−49%; 16%] | 0.203 |
| Number of central apneas | 4.0 | 0.0 | 2.0 | 1.0 | −55% [−92%; 158%] | 0.333 |
| Number of mixed apneas | 3.0 | 0.0 | 3.0 | 1.0 | −25% [−72%; 99%] | 0.521 |
| Number of obstructive apneas | 29.0 | 30.5 | 18.5 | 15.0 | −44% [−69%; 0%] | 0.048 |
| Index of apnea/hypopnea | 23.0 | 22.5 | 20.5 | 17.0 | −14% [−47%; 40%] | 0.533 |
| Index of apnea | 5.0 | 4.0 | 6.5 | 2.5 | −33% [−67%; 38%] | 0.264 |
| Index of hypopnea | 14.0 | 11.0 | 13.0 | 9.5 | −20% [−53%; 36%] | 0.401 |
| Percentage of time with SpO2 < 90% | 10.0 | 11.5 | 9.0 | 3.5 | ND | 0.007 |

ND: Not Done: non parametric test comparing V3 values; estimates with minus sign correspond with improvement in sleep apnea indices.

At end of treatment, there were trends to a lower number of episodes of apnea and hypopnea in the fenofibrate group compared with the placebo group, in particular there was a significant reduction in obstructive apneas (p=0.048).

This was accompanied with a significant reduction with fenofibrate in the percentage of time during sleep with $SpO_2 < 90\%$ (p=0.007).

The improvement in sleep apnea and oxygen saturation indexes was observed in both the patients receiving a statin or not.

Complementary Analyses on the Primary Efficacy Criteria
The results are presented in Table 4.

TABLE 4

| | Placebo | | Fenofibrate 145 mg | | | |
|---|---|---|---|---|---|---|
| | Base. | End (V3) | Base. | End (V3) | Fenofibrate-Placebo | |
| Variables | (median) | (median) | (median) | (median) | Estimate [95% CI] | p |
| Cumulated duration of apnea (min)[a] | 8.0 | 7.5 | 7.0 | 4.5 | −31% [−65%; 37%] | 0.276 |
| Mean duration of apnea (s) | 13.0 | 14.0 | 13.0 | 13.5 | ND | 0.931 |
| Duration of the longest apnea (s) | 24.0 | 30.0 | 21.0 | 23.5 | ND | 0.877 |
| Non cortical micro-awakening per hour[b] | 24.0 | 25.0 | 23.5 | 18.0 | −10.7 [−17.6; −3.8] | 0.004 |

TABLE 4-continued

| Variables | Placebo Base. (median) | Placebo End (V3) (median) | Fenofibrate 145 mg Base. (median) | Fenofibrate 145 mg End (V3) (median) | Fenofibrate-Placebo Estimate [95% CI] | p |
|---|---|---|---|---|---|---|
| Number of non cortical micro-awakening[b] | 172.0 | 167.0 | 142.5 | 128.0 | −75.7 [−126.6; −24.8] | 0.005 |
| $SpO_2$ in wake state (%) | 95.0 | 94.5 | 95.5 | 95.0 | ND | 0.101 |
| Mean of $SPO_2$ on recording (%)[b] | 92.0 | 92.0 | 93.0 | 94.0 | 1.1 [0.2; 2.0] | 0.019 |
| Minimum value of $SpO_2$ (%)[b] | 73.0 | 75.0 | 80.0 | 82.0 | 0.4 [−4.4; 5.2] | 0.859 |
| Percentage time spent with $SpO_2$ < 80% | 0.0 | 0.0 | 0.0 | 0.0 | ND | 0.538 |
| Percentage time spent with $SpO_2$ < 85% | 1.0 | 0.0 | 0.0 | 0.0 | ND | 0.041 |
| Number of tachycardia[a] | 4.0 | 3.05 | 1.5 | 3.0 | 22% [−60%; 268%] | 0.708 |
| Mean duration of tachycardia (s)[a] | 10.0 | 7.5 | 14.0 | 12.0 | 44% [−27%; 184%] | 0.276 |
| Number of bradycardia[a] | 9.0 | 2.0 | 2.0 | 2.5 | 282% [−26%; 1860%] | 0.100 |
| Mean duration of bradycardia (s)[b] | 10.0 | 10.0 | 8.0 | 10.0 | 19.8 [−2.2; 41.7] | 0.074 |
| Mean pulse rate (bpm)[b] | 63.0 | 63.5 | 64.5 | 63.0 | 1.6 [−2.5; 5.7] | 0.427 |
| Standard deviation pulse rate (bpm) | 5.6 | 5.6 | 5.0 | 5.7 | ND | 0.458 |
| Minimum pulse rate (bpm)[b] | 47.0 | 49.0 | 50.0 | 48.5 | 1.7 [−3.1; 6.6] | 0.471 |
| Maximum pulse rate (bpm) | 96.0 | 94.0 | 94.5 | 97.0 | ND | 0.467 |

[a]ANCOVA on Log-transformed data and absolute difference fenofibrate-placebo,
[b]ANCOVA on non-transformed data and relative difference fenofibrate-placebo,
ND: Not Done: non parametric test comparing V3 values; percent estimates with minus sign correspond with improvement.

The number of non cortical micro-awakening indicators related to respiratory events was significantly reduced at the end of treatment by fenofibrate as compared with placebo (p=0.005).

The difference between the groups was also statistically significant for the mean of $SpO_2$ on sleep recording (p=0.019) and for the percentage of time with $SpO_2$<85% (p=0.042). The other variables did not significantly differ between the 2 groups.

Epworth Sleepiness Scale (ESS)

The median of the ESS was 8.5 at baseline and at end of treatment in the fenofibrate group. In the placebo group, it was 7.5 at both assessments.

Computerized Attention/Vigilance Tests

Reflexive visually guided saccades and antisaccades

In the 2 groups, there were no meaningful changes in reflexive visually guided saccades and in reflexive visually guided antisaccades. For none of the parameters assessed were statistically significant differences observed between fenofibrate and placebo.

Reflexive visually guided sustained attention tests

Five (5) consecutive series of tests (sarters) were performed.

The results of the mean of the 5 tests are presented in Table 5.

TABLE 5

| Variables | Placebo Baseline (median) | Placebo End (V3) (median) | Fenofibrate 145 mg Baseline (median) | Fenofibrate 145 mg End (V3) (median) | Fenofibrate-Placebo Estimate [95% CI] | p |
|---|---|---|---|---|---|---|
| Mean latency all sarter (ms)[a] | 404.8 | 411.3 | 432.0 | 409.7 | 3.6 [−20.7; 27.8] | 0.766 |
| Standard Deviation latency all sarters (ms)[a] | 101.4 | 104.2 | 108.1 | 98.0 | 13.2 [−14.8; 41.3] | 0.343 |
| Minimum latency all sarters (ms) | 279.0 | 280.5 | 290.0 | 295.0 | ND | 0.242 |

TABLE 5-continued

| | Placebo | | Fenofibrate 145 mg | | Fenofibrate-Placebo | |
|---|---|---|---|---|---|---|
| | Baseline | End (V3) | Baseline | End (V3) | | |
| Variables | (median) | (median) | (median) | (median) | Estimate [95% CI] | p |
| Maximum latency all sarters (ms)[b] | 791.0 | 769.5 | 770.5 | 750.0 | 7% [−12%; 30%] | 0.491 |
| Percent false responses all sarters | 1.1 | 1.1 | 1.1 | 1.1 | ND | 0.480 |
| Percent omissions all sarters | 0.0 | 0.0 | 0.0 | 0.0 | ND | 0.028 |

[a]ANCOVA on non-transformed data and absolute difference fenofibrate-placebo,
[b]ANCOVA on Log-transformed data and relative difference fenofibrate-placebo,
ND: Not Done: non parametric test on V3 values; percent estimates with minus sign correspond with improvement.

Despite at least half of the patients did not omit any response to the tests, there was a statistically significant reduction in omissions with fenofibrate. The reduction of omissions in this sustained attention test, considered as the most discriminating vigilance test used in this study, is in favor of an improvement of vigilance in patients treated with fenofibrate.

Laboratory Efficacy Variables

The results are summarized in Table 6.

TABLE 6

| | Placebo | | Fenofibrate 145 mg | | Fenofibrate-Placebo | |
|---|---|---|---|---|---|---|
| | Baseline | End (V3) | Baseline | End (V3) | | |
| Variables | (median) | (median) | (median) | (median) | Estimate [95% CI] | p |
| Fasting Triglycerides (mmol/L) | 2.72 | 2.65 | 2.31 | 2.00 | ND | 0.018 |
| Post-Prandial Triglycerides (mmol/L)[a] | 4.77 | 4.68 | 4.03 | 3.27 | −26% [−42%; −7%] | 0.012 |
| Total Cholesterol (mmol/L)[b] | 6.25 | 5.94 | 5.30 | 4.58 | −0.8 [−1.2; −0.33] | 0.001 |
| HDL-Cholesterol (mmol/L)[a] | 0.96 | 1.08 | 0.99 | 1.05 | 2% [−8%; 14%] | 0.662 |
| Fasting Plasma Glucose (mmol/L)[b] | 5.40 | 5.55 | 5.65 | 5.45 | 0.2 [−0.3; 0.7] | 0.324 |
| Fibrinogen (μmol/L)[b] | 10.29 | 10.00 | 10.59 | 8.82 | −1.7 [−2.6; −0.8] | 0.0004 |
| Insulin (pmol/L)[b] | 100.5 | 93.3 | 70.3 | 94.4 | 12.1 [−12.3; 36.6] | 0.318 |

[a]ANCOVA on Log-transformed data and relative difference fenofibrate-placebo,
[b]ANCOVA on non-transformed data and absolute difference fenofibrate-placebo.
ND: Not Done: non parametric test on V3 values; percent estimates with minus sign correspond with improvement.

Fasting TG, post-prandial TG, TC and fibrinogen were significantly reduced by fenofibrate compared with placebo. Fenofibrate had no effect on fasting plasma glucose (FPG). Changes in HDL-C were minor with fenofibrate in patients who had baseline values close to normal. Changes in insulin were highly variable; there was no statistically significant difference between the 2 groups.

Complementary Efficacy Analyses: Correlations Between Changes in TG and Apnea Variables The Pearson test showed statistical significance for the correlation between % change in post-prandial TG and number of apneas ($r=0.507$, $p=0.004$), number of central apneas ($r=0.422$, $p=0.040$), number of mixed apneas ($r=0.364$, $p=0.034$), index of apnea ($r=0.348$, $p=0.044$), and total number of desaturations ($r=0.423$, $p=0.013$) at end of treatment.

The Spearman test was, however, never statistically significant.

Plasma Study Drug Concentration

In the fenofibrate group at V3, (end of treatment), the mean (SD) plasma fenofibric acid level was 6.2 (3.8) μg/mL before dosing and 9.3 (4.0) μg/mL 4 hours after dosing.

Safety Results:

There were no deaths during the study.

One (1) significant adverse event (SAE), for pulmonary embolism, was reported during the run-in period. The patient was not randomized.

One (1) SAE was reported during the treatment period. The patient, in the fenofibrate group, was hospitalized for assessment of metabolic syndrome. This SAE was considered as not related to the study treatment.

No patients prematurely terminated the study because of adverse event (AEs).

One (1) AE was reported in the placebo group and 6 AEs in 3 patients were reported in the fenofibrate group. The AE reported in the placebo group was lumbar pain, and was considered as not related to study treatment. The AEs reported in the fenofibrate group were bloating (n=1), rash (n=1), allergic rhinitis (n=1), metabolic syndrome (SAE, n=1), type 2 diabetes (n=1), and cystitis (n=1).

None of the AEs reported during the treatment period was considered as related to study treatment.

Median % change at end of treatment from baseline in RBC was −4.5% in the placebo group and −2.7% in the fenofibrate group, in hemoglobin: −4.7% and −3.8%, respectively, in hematocrit: −3.9% and −3.2%, in WBC: −12.7% and −11.6%, in platelets: −8.3% and +4.7% (p=0.007), and in creatinine: −9.1% and +5.9% (p=0.015). The other safety biological variables (ALT, AST, CK) did not differ between the 2 groups.

In either treatment group, there were no meaningful changes in mean values of pulse rate, diastolic blood pressure (DBP) or systolic blood pressure (SBP) between baseline and end of treatment. Mean values of body weight and body mass index (BMI) remained roughly unchanged at end of treatment compared to baseline.

4. CONCLUSION

This randomized, placebo-controlled study of 4-week treatment with fenofibrate 145 mg once daily in hypertriglyceridemic obese patients with sleep disturbances not requiring CPAP treatment led to an improvement in most sleep apnea indices with fenofibrate over placebo, in particular a reduction in number of obstructive apneas, and an increase in oxygen saturation during sleep. In parallel, an improvement in attention tests on the next morning was observed. Fenofibrate treatment was well tolerated.

This study shows that fibrates and in particular fenofibrate (or equivalent product that are metobolized by the body in fenofibric acid, such as salts of fenofibric acid) are useful active substances in the treatment of sleep apnea and sleep apnea syndrome, in particular obstructive sleep apnea or obstructive sleep apnea syndrome.

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

The invention claimed is:

1. A method of treating sleep apnea or sleep apnea syndrome in a subject suffering therefrom, said method comprising administering to said subject a pharmacologically effective amount of a fibrate.

2. A method as claimed in claim 1, wherein the sleep apnea is obstructive sleep apnea and the sleep apnea syndrome is obstructive sleep apnea syndrome.

3. A method as claimed in claim 1, wherein said fibrate is fenofibrate.

4. A method as claimed in claim 1, wherein said method of treating sleep apnea or sleep apnea syndrome also improves vigilance in said subject.

5. A method as claimed in claim 1, wherein said fibrate is a choline salt of fenofibric acid.

6. A method as claimed in claim 1, wherein said fibrate is administered orally to said subject.

7. A method as claimed in claim 1, wherein said fibrate is administered daily for at least 30 days.

8. A method as claimed in claim 1, wherein said fibrate is administered in a daily dose equivalent to an amount of from 45 to 235 mg of fenofibric acid.

9. A method as claimed in claim 8, wherein said fibrate is administered in a daily dose equivalent to about 135 mg of fenofibric acid.

10. A method as claimed in claim 1, wherein said fibrate is administered in conjunction with administration of a hydroxymethylglutaryl coenzyme A reductase inhibitor or statin.

11. A method as claimed in claim 10, wherein said hydroxymethylglutaryl coenzyme A reductase inhibitor or statin is selected from the group consisting of pravastatin, lovastatin, simvastatin, atorvastatin, pitavastatin, rosuvastatin and fluvastatin.

12. A method as claimed in claim 1, wherein said fibrate is fenofibrate or a choline salt of fenofibric acid, and wherein said fibrate is administered orally daily for at least 30 days in a daily dose equivalent to an amount of from 45 to 235 mg of fenofibric acid.

13. A method as claimed in claim 12, wherein the sleep apnea is obstructive sleep apnea and the sleep apnea syndrome is obstructive sleep apnea syndrome.

14. A method as claimed in claim 12, wherein said method of treating sleep apnea or sleep apnea syndrome also improves vigilance in said subject.

15. A method as claimed in claim 12, wherein said fibrate is administered in a daily dose equivalent to about 135 mg of fenofibric acid.

16. A method as claimed in claim 12, wherein said fibrate is administered in conjunction with administration of a hydroxymethylglutaryl coenzyme A reductase inhibitor or statin.

* * * * *